(12) United States Patent
Sanchez

(10) Patent No.: US 6,358,966 B2
(45) Date of Patent: Mar. 19, 2002

(54) TREATMENT OF DEPRESSION

(75) Inventor: Connie Sanchez, Glostrup (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 09/809,470

(22) Filed: Mar. 15, 2001

Related U.S. Application Data

(63) Continuation of application No. PCT/DK99/00482, filed on Sep. 14, 1999.

(30) Foreign Application Priority Data

Sep. 15, 1998 (DK) .............................................. 01163/98

(51) Int. Cl.⁷ .............................................. A61K 31/44
(52) U.S. Cl. ...................................................... 514/278
(58) Field of Search ......................................... 514/278

(56) References Cited

U.S. PATENT DOCUMENTS 5,665,725 A * 9/1997 Moltzen et al. .............. 514/278
6,262,061 B1 * 7/2001 Sanchez et al. .............. 514/278

FOREIGN PATENT DOCUMENTS

WO       WO92/22554       12/1992

* cited by examiner

Primary Examiner—William R. A. Jarvis
(74) Attorney, Agent, or Firm—Darby & Darby

(57) ABSTRACT

The compound 1'-[4-[1-(4-fluorophenyl)-1H-indole-3-yl]-1-butyl-spiro[isobenzo-furan-1(3H,4'-piperidine] is active in models predictive of antidepressant effects and is useful for the preparation of a medicament for the treatment of depression or diseases associated with depressive symptoms.

7 Claims, No Drawings

TREATMENT OF DEPRESSION

This is a continuation of international application Serial No. PCT/DK99/00482, filed Sep. 14, 1999, the entire disclosure of which is hereby incorporated by reference.

FIELD OF INVENTION

The present invention relates to the use of the compound 1'-[4-[1-(4-fluorophenyl)-1H-indole-3-yl]-1-butyl]-spiro [isobenzofuran-1(3H),4'-piperidine] or a pharmaceutically acceptable salt thereof for the preparation of medicaments for the treatment of depression.

BACKGROUND OF THE INVENTION

International Patent Publication No. WO 92/22554 describes a series of sigma receptor ligands considered useful for the treatment of a range of psychic and neurological disorders. The structure activity relationship of these compounds has been further investigated by Perregaard, J. et al., *J. Med. Chem.*, 1995, 38, 11, p. 1998–2008.

Among numerous other compounds, said patent publication discloses the compound 1'-[4-[1-(4-fluorophenyl)-1H-indole-3-yl]-1-butyl]-spiro[isobenzofuran-1(3H)4'-piperidine]

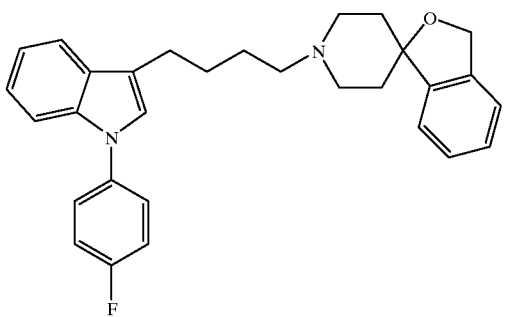

which is the subject of the present invention. This compound was shown in Perregaard, J. et al., *J Med. Chem.*, 1995, 38, 11, p. 1998–2008 to be a potent and selective sigma ligand, in particular a $sigma_2$ ligand. Furthermore, the anxiolytic potential of the compound was tested in the black/white exploration test in rats, which is an animal model predictive for effect in the treatment of generalised anxiety disorder. It was found to be active over a large dose range. Results of further tests in generalised anxiety disorder models are reported in *J Pharmacol. Exp. Ther.*, 1997, 283, No. 2.

Co-pending Danish patent applications Nos. 1267/97, 0071/98 and 0501/98 relate to the hydrochloride of the compound, the effect of the compound in the treatment of addiction to drugs and other substances of abuse and the use of the compound in the treatment of panic attacks, respectively.

Evidence has been presented from studies of the biology and function of sigma receptors that sigma receptor ligands may be useful in the treatment of a range of psychic and neurological disorders, including psychosis and movement disorders, such as dystonia and tardive dyskinesia, and motor disturbances associated with Huntington's chorea or Tourette's syndrome and in Parkinson's disease (Walker, J. M. et al, *Pharmacological Reviews*, 1990, 42, 355). The known sigma receptor ligand, rimcazole, clinically shows effect in the treatment of psychosis (Snyder, S. H., Largent, B. L. *J Neuropsychiatry*, 1989, 1, 7) and a group of sigma receptor ligands have been described to show antihalluci- nogenic activity in animal models (International Patent Publication No. WO 9103243).

Sigma receptor ligands have also been reported to be involved in modulation of NMDA receptor mediated events in the brain and to act as anti-ischemic agents in in vivo tests (Rao, T. S. et al, *Molecular Pharmacology*, 1990, 37, 978). In addition to ischemia, the sigma receptor ligands may also be useful in the treatment of other such NMDA receptor mediated events, e.g. epilepsy and convulsion.

Also, some sigma receptor ligands have been found to show anti-amnesic effects in an animal model (Early et al., *Brain Research*, 1991, 546, 281–286). Sigma ligands have been shown to influence central acetylcholine levels in animal models (Matsuno et al, *Brain Research*, 1992, 575, 315–319; Junien et al, *Eur. J. Pharm.*, 1991, 200, 343–345) and may, therefore, have potential in the treatment of senile dementia of the Alzheimer type.

Finally, some guanidine derivatives having sigma receptor activity have been disclosed to be useful as anxiolytics (International Patent Publication No. WO 9014067) and some sigma receptor ligands have been found to bind to the cocaine binding site on the dopamine transporter and others have been found to inhibit dopamine uptake (Izenwasser, S., et al, *Eur. J Pharmacol*, 243, 201–205 and Woodward, J. J. and Harms, J., *Eur. J Pharmacol.*, 210, 265–270.

Depression is now well recognised as an extremely damaging and invalidating disorder and it has a very large prevalence. It is often associated with suicidal behaviour and people afflicted have a very low quality of life.

Selective serotonin re-uptake inhibitors are now first choice treatments in depression disorders. However, they are only effective after 3–4 weeks of treatment and they are not effective in all patients.

Consequently, there is a need for alternative therapies useful in the treatment of disorders associated with depression.

It has now, surprisingly, been found that the compound of the invention shows a beneficial effect in the treatment of depression.

DESCRIPTION OF THE INVENTION

According to the present invention, a novel use of 1'-[4-[1-(4-fluorophenyl)-1H-indole-3-yl]-1-butyl]-spiro [isobenzo-furan-1(3H),4'-piperidine], namely for the preparation of a medicament useful in the treatment depression is provided.

The term depression contemplates all diseases and conditions which are associated with depression including those classified in the IDC-10 and DSM-IV rating scales. Such diseases or disorders comprise major depression, dysthymic disorder, depressive episodes of bipolar disorders and depressive episodes associated with other mood disorders, including seasonal mood disorders and mood disorders due to a general medical condition and substance induced mood disorder.

The term "treatment of depression" covers relief of symptoms, cure or prevention of the disease or condition.

According to the invention, the compound 1'-[4-[1-(4-fluorophenyl)-1H-indole-3-yl]-1-butyl]-spiro[isobenzo-furan-1(3H),4'-piperidine] may be used as the base of the compound or as a pharmaceutically acceptable acid addition salt thereof or as an anhydrate or hydrate of such salt. The salts of the compound used in the invention are salts formed with non-toxic organic or inorganic acids. Exemplary of such organic salts are those with maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic and theophylline acetic acids, as well as the 8-halotheophyllines, for example 8-bromo-theophylline. Exemplary of such inorganic salts are those with hydrochloric, hydrobromic, sulfuric, sulfamic, phosphoric and nitric acids. Preferably, the compound is used as the base, the hydrochloride or the fumarate.

Chronic administration of the compounds used in the method of the invention has been found to cause a reversal of anhedonia induced by chronic mild stress in rats in the chronic mild stress (CMS) model. The CMS-model is a well recognised model of depression (Willner, Paul, Psycopharmacology, 1997, 134, 319–329.)

According to the invention, 1'-[4-[1-(4-fluorophenyl)-1H-indole-3-yl]-1-butyl]-spiro[isobenzofuran-1(3H),4'-piperidine], or a pharmaceutically acceptable salt thereof, may be administered in any suitable way such as orally or parenterally, and it may be presented in any suitable form for such administration, for example in the form of tablets, capsules, powders, syrups or solutions or dispersions for injection. Preferably, and in accordance with the purpose of the present invention, the compound of the invention is administered in the form of a solid pharmaceutical entity, suitably as a tablet or a capsule or in the form of a suspension, solution or dispersion for injection.

Methods for the preparation of solid pharmaceutical preparations are well known in the art. Tablets may thus be prepared by mixing the active ingredients with ordinary adjuvants and/or diluents and subsequently compressing the mixture in a convenient tabletting machine. Examples of adjuvants or diluents comprise: corn starch, lactose, talcum, magnesium stearate, gelatine, lactose, gums, and the like. Any other adjuvant or additive such as colourings, aroma, preservatives, etc. may also be used provided that they are compatible with the active ingredients.

The compound of the invention is most conveniently administered orally in unit dosage forms such as tablets or capsules, containing the active ingredient in an amount from about 10 $\mu$g/kg to 10 mg/kg body weight, preferably 25 $\mu$g/day/kg to 2.0 mg/day/kg, most preferably 0.1 mg/day/kg to 1.0 mg/day/kg body weight.

The fumarate of 1'-[4-[1-(4-fluorophenyl)-1H-indole-3-yl]-1-butyl]-spiro[isobenzo-furan-1(3H),4'-piperidine] can be prepared as described in Perregaard, J. et al., *J. Med. Chem.*, 1995, 38, 11, 1998–2008 (compound 14f) and the base and other pharmaceutically acceptable salts may be obtained therefrom by standard procedures.

Thus the acid addition salts according to the invention may be obtained by treatment of 1'-[4-[1-(4-fluorophenyl)-1H-indole-3-yl]-1-butyl]-spiro[isobenzo-furan-1(3H),4'-piperidine] with the acid in an inert solvent followed by precipitation, isolation and optionally re-crystallisation by known methods and if desired micronisation of the crystalline product by wet or dry milling or another convenient process, or preparation of particles from a solvent-emulsification process.

Precipitation of the salt is preferably carried out in an inert solvent, e.g. an inert polar solvent such as an alcohol (e.g. ethanol, 2-propanol and n-propanol).

Pharmacological Tests

The model of chronic mild stress induced anhedonia in rats.

The effect of the compound of the invention in the treatment of depression was tested in the model of chronic mild stress induced anhedonia in rats. This model is based on the observation that chronic mild stress causes a gradual decrease in sensitivity to rewards, for example consumption of sucrose, and that this decrease is dose-dependently reversed by chronic treatment with antidepressants. The method has previously been described and more information with respect to the test appears from Willner, Paul, Psycopharmacology, 1997, 134, 319–329.

Experimental Procedure

Male Wistar rats were trained to consume a 1% sucrose solution by nine 1-hour baseline tests in which sucrose was presented in the home cage following 14 h food and water deprivation.

One group of animals was subjected to a chronic mild stress procedure for a period of 9 consecutive weeks. Each week of the stress regime consisted of two periods of food and water deprivation, two periods of 45-degree cage tilt, two periods of intermittent illumination (light on and off every 2 h), two periods of soiled cage (250 ml water saw dust bedding), two periods of paired housing, two periods of low stroboscobic illumination (150 flashes/min) and two periods of no stress. All stress periods were of 12–14 hours duration and followed continuously, day and night. Control animals were housed in separate rooms with food and water freely available except for a 14-h period preceding each sucrose test, and they had no contact with stressed animals.

Stressed animals as well as control animals were divided into matched subgroups, and for subsequent five weeks they received daily intraperitoneal injections (1 ml/kg body weight) of vehicle (minimum amount of propylene glycol and methane sulfonic acid (1:1) diluted with water) or test compound. Sucrose tests were carried out 24 hours following to last drug treatment.

Results

In the final baseline test, all animals consumed about 16 g sucrose solution. After three weeks the intake remained at 14 g in the control group whereas it fell to about 9.5 g in stressed animals. These levels persisted for the remainder of the 9-week period resulting in a significant group effect.

The compound of the invention did not significantly affect the consumption of sucrose in the control animals.

The compound of the invention was able to reverse the chronic mild stress induced deficit in sucrose intake at a dose of 1.0 mg/kg . In stressed animals treated with 1.0 mg/kg intake was significantly increased from initial scores after three, four and five weeks and at the end of the treatment period the sucrose intake did not significantly differ from that of vehicle treated controls (p=0.130) and it was significantly higher than that of vehicle treated stressed animals (p=0.003).

Citalopram, a well known serotonin re-uptake inhibitor, was included in the tests for comparison purposes. Citalopram (10 mg/kg) did not significantly affect the consumption of sucrose in the control animals whereas it was able to reverse the chronic mild stress induced deficit in sucrose. The increase in intake in stressed animals was significantly increased from initial scores after two weeks and maintained thereafter. At the end of the treatment period the sucrose intake did not significantly differ from that of vehicle treated controls (p=0.177) and it was significantly higher than that of vehicle treated stressed animals (p=0.001).

What is claimed is:

1. A method of treating depression, comprising administering the compound 1-[4-[1-(4-fluorophenyl)-1H-indole-3-yl]-1-butyl]-spiro[isobenzo-furan-1(3H),4'-piperidine] or a pharmaceutically acceptable salt thereof, to a person in need thereof.

2. The method of claim 1, wherein the compound is used in the form of the base, the fumarate or the hydrochloride.

3. The method of claim 1, wherein the compound is administered as a unit dose.

4. The method of claim 3, wherein the unit dose comprises the compound in an amount from about 10 µg/kg to 10 mg/kg body weight.

5. The method of claim 4, wherein the unit dose comprises the compound in an amount from 25 µg/day/kg to 2.0 mg/day/kg body weight.

6. The method of claim 4, wherein the unit dose comprises the compound in an amount from 0.1 mg/day/kg to 2.0 mg/day/kg body weight.

7. The method of claim 1, wherein the depression is selected from the group consisting of major depression, dysthymic disorder, depressive episodes of bipolar disorders, and depressive episodes associated with other mood disorders.

* * * * *